United States Patent
Rigal et al.

(10) Patent No.: US 8,563,704 B2
(45) Date of Patent: Oct. 22, 2013

(54) PEPTIDE APTAMER FOR NEUTRALIZING THE BINDING OF PLATELET ANTIGEN SPECIFIC ANTIBODIES AND DIAGNOSTIC AND THERAPEUTIC APPLICATIONS CONTAINING THE SAME

(75) Inventors: Dominique Rigal, Lyons (FR); Julien Thibaut, Lyons (FR); Gemain Gillet, Lyons (FR); Yves Merieux, Lyons (FR)

(73) Assignee: Stiftung für Diagnostische Forschung, Cressier sur Morat (CH)

( * ) Notice: Subject to any disclaimer, the term of this patent is extended or adjusted under 35 U.S.C. 154(b) by 0 days.

(21) Appl. No.: 13/449,990

(22) Filed: Apr. 18, 2012

(65) Prior Publication Data
US 2012/0245338 A1   Sep. 27, 2012

Related U.S. Application Data

(62) Division of application No. 12/278,475, filed as application No. PCT/EP2007/001042 on Feb. 7, 2007, now Pat. No. 8,183,055.

(30) Foreign Application Priority Data

Feb. 7, 2006   (EP) .................................... 06002496

(51) Int. Cl.
*C12N 15/115* (2010.01)
*C12N 15/62* (2006.01)
*A61K 38/00* (2006.01)

(52) U.S. Cl.
USPC ........................................ 536/23.4; 530/300

(58) Field of Classification Search
None
See application file for complete search history.

(56) References Cited

FOREIGN PATENT DOCUMENTS

WO   WO94/11740 A1   5/1994

OTHER PUBLICATIONS

Jeong, H., et al., "Genomic blueprint of Hahella chejuensis, a marine microbe producing and algicidal agent", Nucleic Acids Research, 2005, 33(22):7066-7073.
Rigal, D., "Lyophilized platelets (Lyo P) used for the detection of HPA antibodies by MAIPA assay", Vox Sanguinis, Jul. 2005, 89(Supp 1):23.
Uniprot Database Accession No. Q2SHY4 (Jan. 24, 2006, XP002442167).
Jeong, Haeyoung, et al., "Genomic Blueprint of Hahella Chejuensis, a Marine Microbe Producing an Algicidal Agent," Nucleic Acids Research, 2005, vol. 33, No. 22, pp. 2-9.
Uniprot submission Q2SHY4. Jan. 2006. [Retrieved from the Internet Jan. 27, 2012: <URL: http://www.uniprot.org/uniprot/q2shy4>].

*Primary Examiner* — Julie Ha
*Assistant Examiner* — Li Ni Komatsu
(74) *Attorney, Agent, or Firm* — McDonnell Boehnen Hulbert & Berghoff LLP

(57) ABSTRACT

The present invention relates to a peptide aptamer which mimics particularly the human platelet antigen HPA-Ia epitope present on the platelet GPIIb/IIIa molecules and which is capable of neutralizing the binding of HPA-I a specific antibodies (anti-HPA-1 a). This peptide aptamer is advantageously used in a method for detecting and identifying HPA-I a specific antibodies in human serum, in a diagnostic kit for screening and identifying antibodies, in an immunoassay and a pharmaceutical composition.

3 Claims, 13 Drawing Sheets

Figures 1A, 1B:
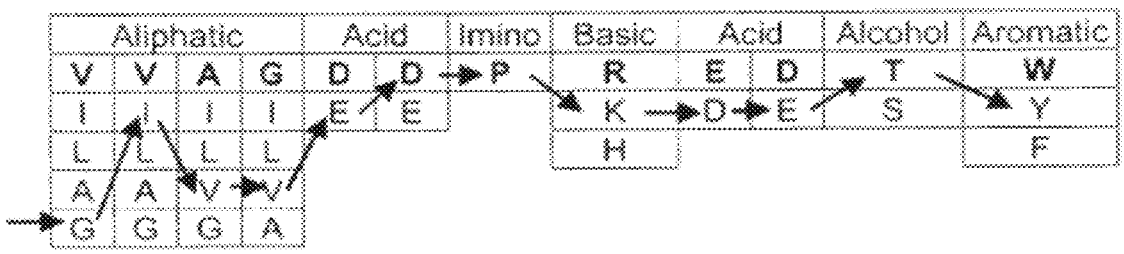

MMSDKIIHLTDDSFDTDVLKADGAILVDFWAEWCGPVVAGDDPREDTWGPCKMIAPILDEIADEYQG
　　　　Thioredoxin N-term　　　　　　　　　dodecapeptide
KLTVAKLNIDQNPGTAPKYGIRGIPTLLLFKNGEVAATKVGALSKGQLKEFLDANLVDLQHHHHHH
　　　　　　Thioredoxine C-term.　　　　　　　　　　　　　　　　　　6 x His

Fig. 3b

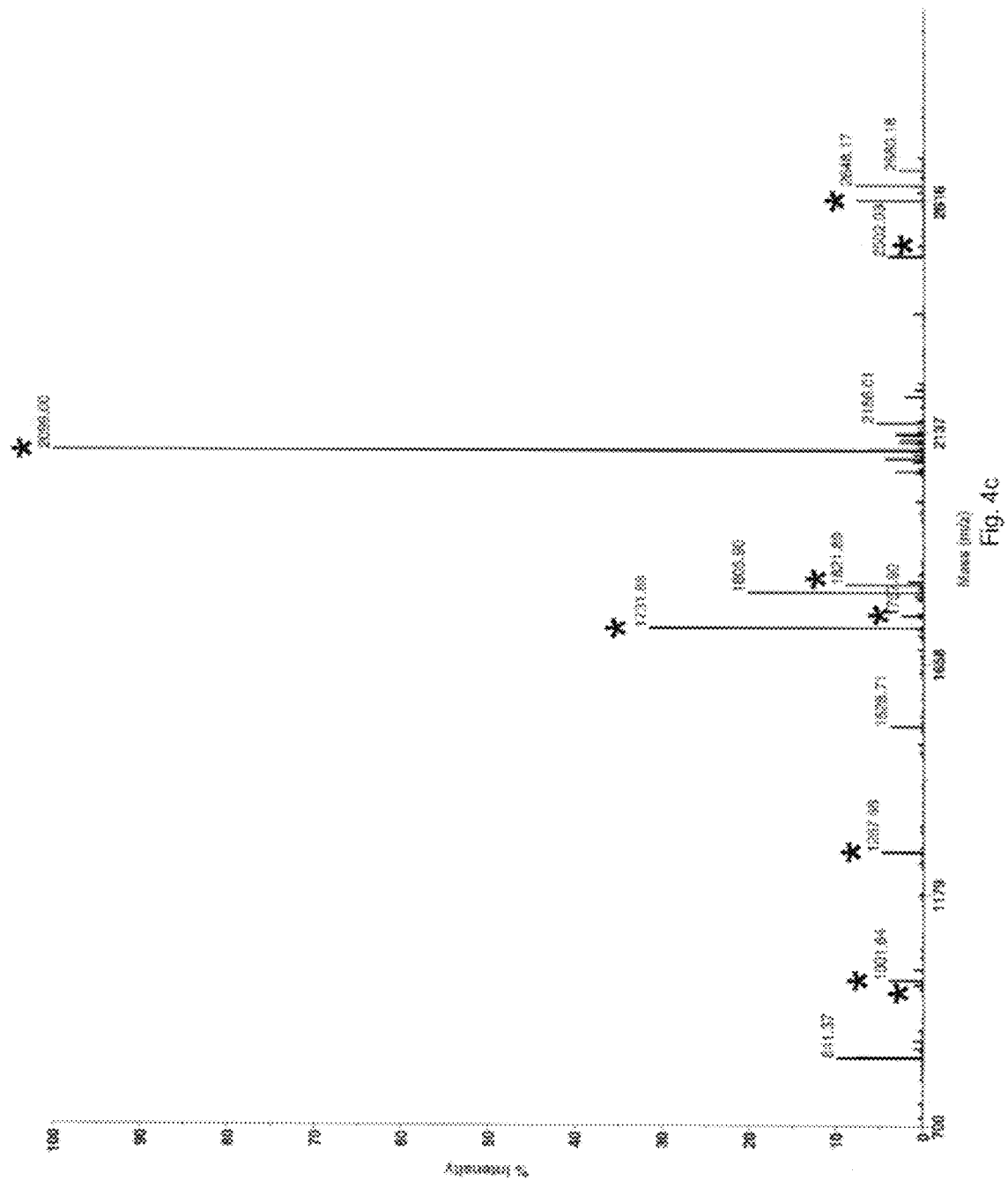

SEQUENCE LISTING

<160> NUMBER OF SEQ ID NOS: 7

<210> SEQ ID NO 1
<211> LENGTH: 12
<212> TYPE: PRT
<213> ORGANISM: Artificial
<220> FEATURE:
<223> OTHER INFORMATION: Synthetic; synthetically or recombinantly
      produced peptide

<400> SEQUENCE: 1

Val Val Ala Gly Asp Asp Pro Arg Glu Asp Thr Trp
1               5                   10

<210> SEQ ID NO 2
<211> LENGTH: 133
<212> TYPE: PRT
<213> ORGANISM: Homo sapiens

<400> SEQUENCE: 2

Met Met Ser Asp Lys Ile Ile His Leu Thr Asp Asp Ser Phe Asp Thr
1               5                   10                  15

Asp Val Leu Lys Ala Asp Gly Ala Ile Leu Val Asp Phe Trp Ala Glu
            20                  25                  30

Trp Cys Gly Pro Val Val Ala Gly Asp Pro Arg Glu Asp Thr Trp
        35                  40                  45

Gly Pro Cys Lys Met Ile Ala Pro Ile Leu Asp Glu Ile Ala Asp Glu
    50                  55                  60

Tyr Gln Gly Lys Leu Thr Val Ala Lys Leu Asn Ile Asp Gln Asn Pro
65              70                  75                  80

Gly Thr Ala Pro Lys Tyr Gly Ile Arg Gly Ile Pro Thr Leu Leu Leu
                85                  90                  95

Phe Lys Asn Gly Glu Val Ala Ala Thr Lys Val Gly Ala Leu Ser Lys
            100                 105                 110

Gly Gln Leu Lys Glu Phe Leu Asp Ala Asn Leu Val Asp Leu Gln His
        115                 120                 125

His His His His His
        130

<210> SEQ ID NO 3
<211> LENGTH: 405
<212> TYPE: DNA
<213> ORGANISM: Homo sapiens

<400> SEQUENCE: 3
catatgatga gcgataaaat tattcacctg actgacgaca gttttgacac ggatgtactc     60
aaagcggacg gggcgatcct cgtcgatttc tgggcagagt ggtgcggtcc ggttgtggcg    120
ggggatgacc ctcgggagga tacgtggggt ccgtgcaaaa tgatcgcccc gattctggat    180
gaaatcgctg acgaatatca gggcaaactg accgttgcaa aactgaacat cgatcaaaac    240
cctggcactg cgccgaaata tggcatccgt ggtatcccga ctctgctgct gttcaaaaac    300
ggtgaagtgg cggcaaccaa agtgggtgca ctgtctaaag gtcagttgaa agagttcctc    360
gacgctaacc tggtcgacct gcagcaccat caccatcacc attaa                    405

<210> SEQ ID NO 4
<211> LENGTH: 12
<212> TYPE: PRT
<213> ORGANISM: Artificial
<220> FEATURE:
<223> OTHER INFORMATION: Synthetic; synthetically or recombinantly
      produced peptide

<400> SEQUENCE: 4

Gly Ile Val Val Glu Asp Pro Lys Asp Glu Thr Tyr
1               5                   10

<210> SEQ ID NO 5
<211> LENGTH: 18
<212> TYPE: DNA
<213> ORGANISM: Artificial
<220> FEATURE:
<223> OTHER INFORMATION: Synthetic; Primer for DNA sequencing

<400> SEQUENCE: 5
attcacctga ctgacgac                                                    18

<210> SEQ ID NO 6
<211> LENGTH: 19
<212> TYPE: DNA

-continued

```
<213> ORGANISM: Artificial
<220> FEATURE:
<223> OTHER INFORMATION: Synthetic; PCR primer with SalI site

<400> SEQUENCE: 6
tgtcgaccag gttagcgtc                                               19

<210> SEQ ID NO 7
<211> LENGTH: 23
<212> TYPE: DNA
<213> ORGANISM: Artificial
<220> FEATURE:
<223> OTHER INFORMATION: Synthetic; PCR primer with NdeI site

<400> SEQUENCE: 7
tcatatgatg agcgataaaa tta                                          23
```

PEPTIDE APTAMER FOR NEUTRALIZING THE BINDING OF PLATELET ANTIGEN SPECIFIC ANTIBODIES AND DIAGNOSTIC AND THERAPEUTIC APPLICATIONS CONTAINING THE SAME

CROSS REFERENCE TO RELATED APPLICATIONS

This application is a divisional of U.S. patent application Ser. No. 12/278,475, filed Oct. 15, 2008 (now U.S. Pat. No. 8,183,055), which is a 35 U.S.C. 371 National Application of PCT/EP2007/001042, filed Feb. 7, 2007, which claims priority to European Patent Application Number 06002496.5, filed Feb. 7, 2006.

DESCRIPTION

The present invention relates to a peptide aptamer which mimics particularly the human platelet antigen HPA-1a epitope present on the platelet GPIIb/IIIa molecules and which is capable of neutralizing the binding of HPA-1a specific antibodies (anti-HPA-1a). This peptide aptamer is advantageously used in a method for detecting and identifying HPA-1a specific antibodies in human serum, in a diagnostic kit for screening and identifying antibodies, in an immunoassay and a pharmaceutical composition.

Platelets are one of the primary components of human blood and are the cellular components of the blood coagulation system. Blood is basically made up of plasma, red blood cells (erythrocytes), white blood cells (leukocytes), and platelets (thrombocytes). Platelets are produced in the bone marrow by megakaryocytes. It is commonly understood that platelets are actually not true cells, but are fragments of membrane and cytoplasm containing granules. More specifically, platelets comprise an outer membrane and cytoplasm from megakaryocytes which in turn contain granules, dense bodies, a dense tubular system, and mitochondria.

Besides the platelet glycoproteins GPIIb/IIIa, GPIa/IX, GPIa/IIa or GPIV, platelets contain at least five glycoproteins that are linked by glycosyl phosphatidylinositol (GPI)-anchors. Among these is a 170-kDa glycoprotein which is classified as CD109. CD 109 is characterized by carrying inter alia the Gov alloantigen.

Immune thrombocytopenia is a clinical status in which the platelets are destroyed by antibodies. Idiopathic thrombocytopenia purpura (ITP) is a common disorder characterized by autoimmune platelet destruction caused by IgG antiplatelet autoantibodies targeting GPIIb/IIIa, GPIa/IX, GPIa/IIIa or GPIV platelet glycoproteins. Neonatal/fetal alloimmune thrombocytopenia (NAIT) is caused by maternal human platelet alloantigen (HPA) alloantibodies (anti-HPA) which destroy fetal platelets provoking a severe thrombocytopenia. NAIT has an estimated incidence of 1/1000 pregnancies and provides in utero cerebral bleeds or ventriculomegaly. The screening and the identification of alloantibodies is a mandatory step to prevent and cure this disease. Post-transfusion purpura (PTP) is another immune mediated destruction of platelets due to anti-HPA alloantibodies. Platelet refractoriness is a clinical situation in which transfused platelets are destroyed by alloantibodies produced by the recipient. The characterization of these antibodies is a necessary step to provide efficient platelet transfusion.

Up to now, all methods for detecting auto- or alloantibodies directed to platelets use fresh platelets in immunoblotting, immunoprecipitation, immunocapture, platelet immunofluorescent tests, or monoclonal antibody immobilization of platelet antigens such as monoclonal antibody immobilization platelet assay (MAIPA), or enzyme-linked immunosorbent assay (ELISA). All these assays require a collection of typed platelets in the HPA systems beforehand. Moreover, these assays known in the art use fresh platelets, as outlined above. However, during their conservation at 4° C. or −20° C., the platelets' glycoproteins undergo a shedding process so that the platelet preparation is inappropriate to detect some platelet antibodies. All the attempts to keep a normal level of the platelet glycoprotein expression for a longer period of time, such as more than one week, were not successful. Due to these facts, it is necessary to collect a new batch of platelets from the donors every week. Thus, there is a constant need in the field of platelet immunology for a method of keeping a normal level of platelet glycoprotein expression during a long period of time (e.g. more than one month).

Thus, the technical problem underlying the present invention is to provide a novel system enabling the detection and/or identification of human platelet antigen specific antibodies in human serum. In particular, the present invention should provide (i) an aptamer which retains its epitope expression of the platelet alloantigens present on platelet glycoproteins,—i.e. the normal level and preferably also the normal pattern—stably under storage, (ii) a process for producing such stable aptamers, and (iii) analytical, especially immunological applications of such stable aptamers.

The solution to the above technical problem is achieved by providing the embodiments characterized in the claims.

In particular, there is provided a peptide aptamer comprising:
(A) at least one dodecapeptide having in the direction from N-terminus to C-terminus a sequence of
   (i) four aliphatic amino acids selected from the group consisting of valine, isoleucine, leucine, alanine and glycine,
   (ii) two acid amino acids selected from the group consisting of aspartic acid and glutamic acid,
   (iii) one proline,
   (iv) one basic amino acid selected from the group consisting of arginine, lysine and histidine,
   (v) two acid amino acids selected from the group consisting of aspartic acid and glutamic acid,
   (vi) one alcohol amino acid selected from the group consisting of threonine and serine and
   (vii) one aromatic amino acid selected from the group consisting of tryptophane, tyrosine and phenylalanine;
(B) at least one polypeptide; and optionally
(C) one or more detectable marker(s).

The term "peptide aptamer" as used herein also includes any compound as defined above, wherein the dodecapeptide functions as a hapten. Further, the peptide aptamer according to the present invention is capable of mimicking the HPA-1a epitope present on platelet glycoproteins GPIIb/IIIa.

According to the present invention, the term "dodecapeptide" includes any dodecapeptides having an amino acid sequence as defined above or explained in FIGS. 1a and 1b. In particular, the dodecapeptide may be bound to one or more polypeptides via any bonding mode, e.g. via covalent, hydrogen bridge, van-der-Waals or electrostatic bond(s). In a preferred embodiment of the present invention, the dodecapeptide is covalently linked to the polypeptide.

In one embodiment of the present invention, the peptide aptamer as defined above comprises a dodecapeptide having the sequence VVAGDDPREDTW (SEQ ID NO: 1).

Further, herein, the term "polypeptide" is not limiting with respect to sequence length or type, but includes any suitable amino acid sequence, such as sequences of scaffold proteins or fusion proteins. According to the present invention, said polypeptide(s) may also be used in the present invention in form of their fragments and may contain any residue originating from their preparation, such as labels used for detection or in any purification step. The polypeptide(s) according to the present invention also include(s) such polypeptide(s) having alterations originating from contact with a biological environment, such as glycosylation, adhesion of nucleic acids or any other chemical modification.

In another embodiment of the present invention, the peptide aptamer as defined above comprises a polypeptide selected from the group consisting of thioredoxin (Trx), green fluorescent protein (GFP), *Staphylococcal* nuclease, coiled coil polypeptides and cysteine-containing polypeptides able to form disulfide bridges.

The polypeptide(s) according to the present invention may function as an inert carrier, a scaffold protein useful for presenting the dodecapeptide to the antibody, a purification aid useful for purifying the peptide aptamer or a detection means useful in detecting the peptide aptamer.

According to the present invention, the above defined dodecapeptide(s) may be bound to any position of the polypeptide(s). For example, the dodecapeptide(s) may be bound to the N-terminus or to the C-terminus of the polypeptide(s) or may be incorporated within the polypeptide resulting in two fragments flanking the N- and C-terminus of said dodecapeptide. It is further possible that the peptide aptamer according to the present invention contains two or more dodecapeptides which may be bound to the same or to different locations of said polypeptide(s) or to fragments thereof. In a further embodiment of the present invention, the peptide aptamer contains two or more dodecapeptides bound to each other, directly or via a peptide spacer.

The term "detectable marker" as used herein is not restricted to a special type of detection marker, such as biochemical detection marker, but includes any residue known in the art which is suitable for detection.

In one embodiment of the present invention, the peptide aptamer as defined above, comprises a detectable marker selected from the group consisting of fluorescent marker, radioactive marker, His-tag, glutathione transferase (GST), Flag-tag, biotin, Ha-tag, Myc-tag and XPress-tag.

Figure 3A:
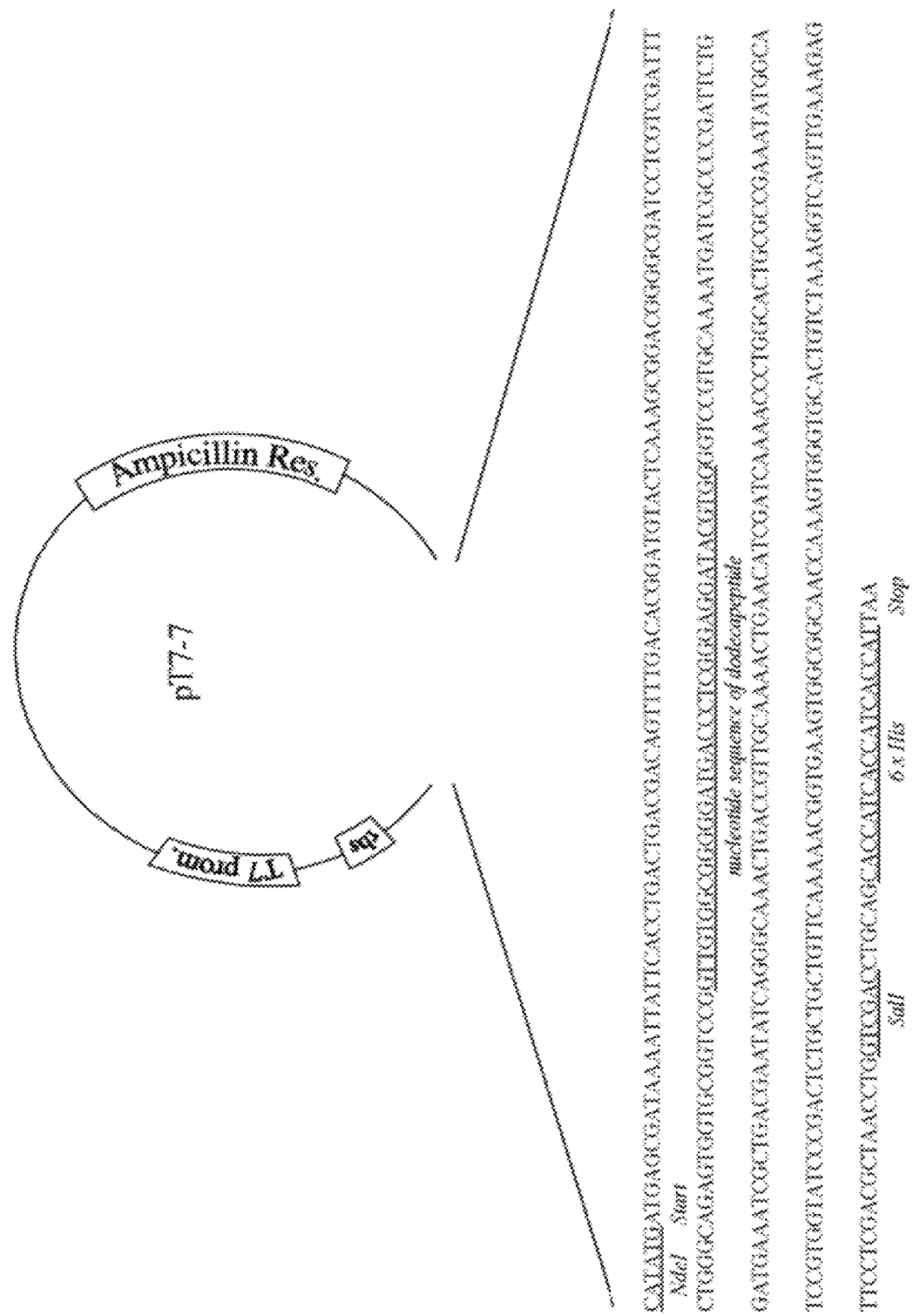

As used herein, the term "thioredoxin-human-platelet-antigen 1a" (Trx-HPA-1a) relates to a preferred embodiment of the present invention, wherein the peptide aptamer as defined above comprises a dodecapeptide according to SEQ ID NO:1, fused into the active site of the polypeptide thioredoxin (Trx), with said Trx having as a detection marker a His-tag (FIGS. 3a and 3b). Said Trx-HPA-1a has a protein sequence according to SEQ ID NO: 2 (FIG. 3b) and is encoded by the nucleic acid sequence SEQ ID NO: 3 (FIG. 3a).

The peptide aptamer of the present invention can be prepared by any method known in the art, such as recombinant DNA technology.

A further embodiment of the present invention relates to a method for detecting or identifying human platelet antigen specific antibodies, comprising the steps of
(i) providing a human serum to be tested for human platelet specific antibodies;
(ii) bringing into contact the human serum with the peptide aptamer as defined above; and
(iii) detecting direct or indirect interaction of the peptide aptamer with human platelet antigen specific antibody.

Herein, the term "human platelet antigen" includes the HPA-1a epitope present on the platelet GPIIb/IIIa glycoprotein but also the soluble HPA-1a epitope present on the soluble form of this GPIIb/IIIa in the serum or in any fluids of the body, Herein, the term "human platelet antigen specific antibody" includes any HPA-1a specific antibody (anti-HPA-1a) and also those antibodies which have a cross-reactivity with other proteins or glycoproteins.

As used herein, the term "human serum" includes any human blood serum, plasma or amniotic fluid obtained either directly from a patient or from stored blood.

According to the present invention, the expression "direct or indirect interaction" includes any interaction between the peptide aptamer and the human platelet antigen specific antibody and further includes any interaction, wherein other molecules are involved. Such other molecules may be for example proteins, protein complexes, nucleic acids, sugars and/or lipids.

The detecting step (iii) of the above-defined method comprises one or more detection method(s) selected from the group consisting of immunoblotting, immunoprecipitation, immunocapture, monoclonal antibody immobilization of platelet antigens or enzyme linked immuno sorbent assay (ELISA), flow cytometry, protein array technology, spectroscopy, mass spectrometry, chromatography, surface plasmonic resonance, fluorescence extinction and/or fluorescence energy transfer.

In a preferred embodiment of the present invention, the antibody to be detected or identified in the above-defined method is anti-HPA-1a.

In another embodiment of the present invention, the method as defined above may be employed for detecting and/or identifying human platelet antigen specific antibodies in the serum of a patient suffering from a form of immune thrombocytopenia.

In a preferred embodiment of the present invention, the method as defined above is used for detecting and/or identifying human platelet antigen specific antibodies in the serum of a patient, wherein the patient suffers from immune thrombocytopenia, selected from the group consisting of ideopathic thrombocytopenia purpura (ITP), neonatal/fetal alloimmune thrombocytopenia (NAIT), post-transfusion purpura (PTP) or platelet refractoriness.

A further embodiment of the present invention relates to a diagnostic kit for screening and identifying human platelet antigen specific antibodies, comprising the peptide aptamer according to the present invention. The diagnostic kit may contain any further ingredients/compounds known in the art for carrying out the screening or identifying procedures.

Another embodiment of the present invention relates to an immunoassay for the detection of human platelet antigen specific antibodies in human serum, comprising the peptide aptamer according to the present invention. Examples of such immunoassays are immunoblotting, immunoprecipitation, immunocapture, monoclonal antibody immobilization of platelet antigens, enzyme linked immuno sorbent assay (ELISA) and/or radioimmunoassay. Further assays relate to surface plasmonic resonance, fluorescence evanescence and flow cytometry.

A further embodiment according to the present invention relates to a pharmaceutical composition, comprising a therapeutically effective amount of the peptide aptamer according to the present invention and optionally one or more additional components selected from the group consisting of a pharmaceutically acceptable carrier, pharmaceutically acceptable salts, an auxiliary agent, a diluent and a solvent, or any combination thereof.

Moreover, the pharmaceutical composition can be administered in a suitable dosage from 5 to 50 mg via any appropriate route such as parenterally, orally, cutaneously or sublingually or injected into a lymphoid organ to a patient in need thereof.

The pharmaceutical composition of the present invention can be used for the treatment and/or prevention of immune thrombocytopenia disorders such as ideopathic thrombocytopenia purpura (ITP), neonatal/fetal alloimmune thrombocytopenia (NAIT), post-transfusion purpura (PTP) or platelet refractoriness. This aptamer could be used to neutralize the anti-HPA-1a antibodies in the plasma of mothers, it could be injected into the foetus or into the amniotic fluid. Moreover, this aptamer could be grafted on support like beads or polymers to deplete the antibodies when the plasma is incubated with these supports during an apheresis procedure (selective plasma apheresis).

The figures show:

FIG. 1 shows (a) the amino acid combinations of the dodecapeptide (SEQ ID NO:1) comprised in the peptide aptamer according to the present invention. All sequences contain in this order: 4 aliphatic amino acids (V, I, L, A, G), 2 acid amino acids (D, E), 1 proline, 1 basic amino acid (R, K, H), 2 acid amino acids (D, E), 1 alcohol amino acid (T, S) and 1 aromatic amino acid (W, Y, F). The arrow indicates the direction from N-terminus to C-terminus of the peptide. (b) a random example of a dodecapeptide according to the present invention. The arrows indicate the direction of sequence from N-terminus to C-terminus. The resulting dodecapeptide of the example has the peptide sequence Gly-Ile-Val-Val-Glu-Asp-Pro-Lys-Asp-Glu-Thr-Tyr (SEQ ID NO:4).

Figure 2:
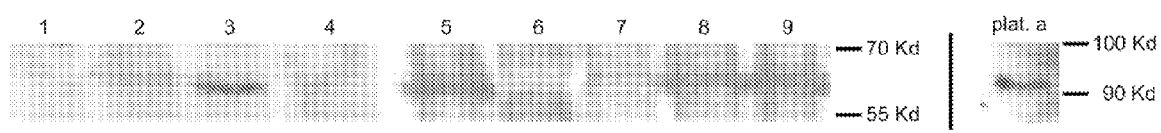

FIG. 2 shows Western blotting probed with the Camtran monoclonal antibody. Whole protein extracts from selected bacterial clones (1-9). A sample from HPA-1a platelets was used as a positive control (left lane, "plata"). Positive clones are characterized by a 63 kD band (lanes 2, 3, 5, 8, 9).

FIG. 3 shows (a) the sequence (SEQ ID NO:3) encoding the Trx-HPA-1a protein. This ORF is cloned between NdeI and SalI restriction sites of the pT7-7 expression vector. The Trx-HPA-1a protein possesses a 6-His tail at its C-terminal end. (b) the sequence (SEQ ID NO:2) of the Trx-HPA-1a protein. The protein contains a 12 amino acid long sequence in the active site of the thioredoxin, as well as a poly-histidine tail at the C-terminal end.

Figure 4A:
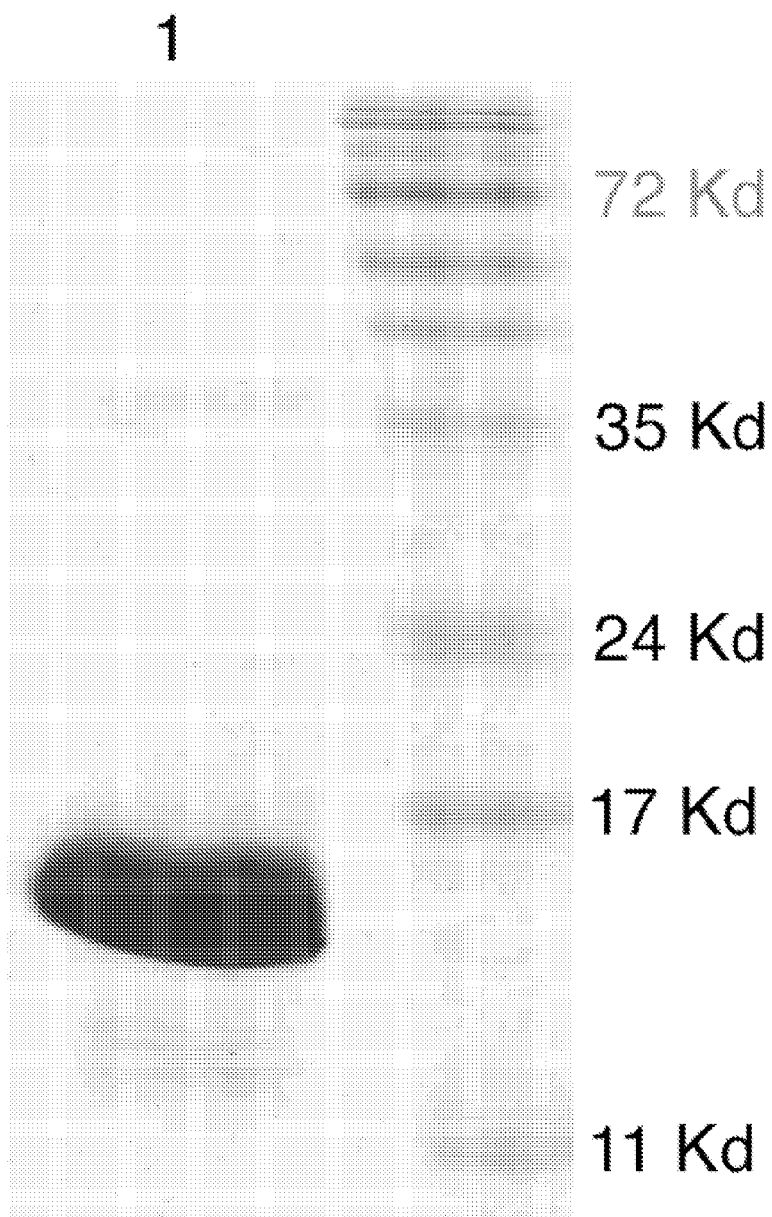
Figure 4B:
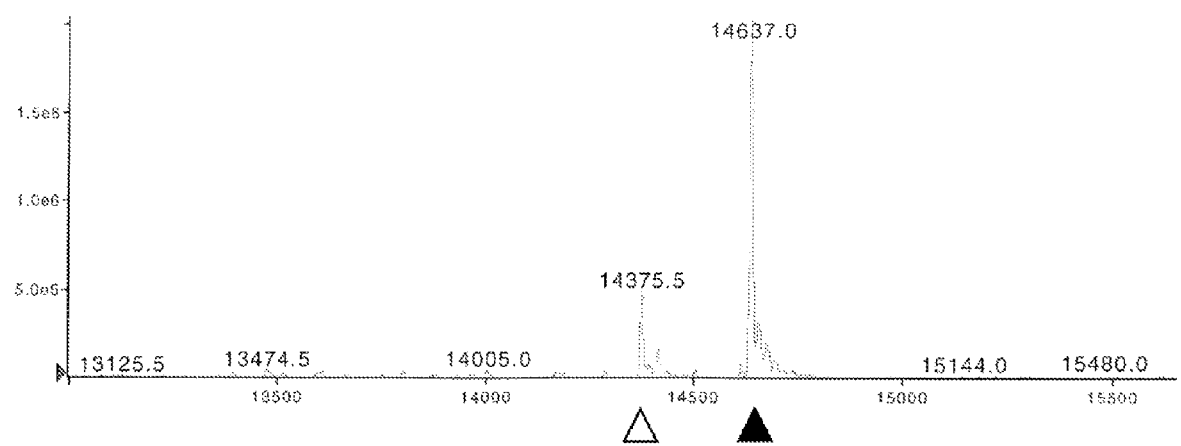

FIG. 4 shows (a) the detection of the recombinant protein by SDSPage (Coomassie blue). 20 μg of the protein purified by anion exchange chromatography were electrophoresed on a 20% polyacrylamide gel (lane 1). Molecular weight markers are shown on the right. (b) the electrospray mass spectrum of the Trx-HPA-1a protein. A major peak at expected size (14 640 da) is detected. The minor peak (D) corresponds to Trx-HPA-1a lacking two methionone residues at the N-term end. (c) the MALDI-TOF mass spectrometry spectrum of the products obtained after tryptic digestion of of Trx-HPA-1a. Black stars (H) correspond to peaks at expected size. Together these peaks correspond to 80% of the Trx-HPA-1a sequence.

Figure 5:
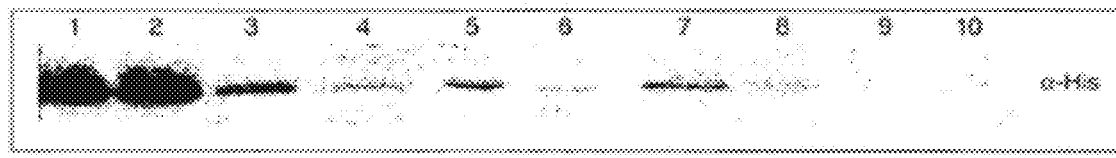
Figure 9:
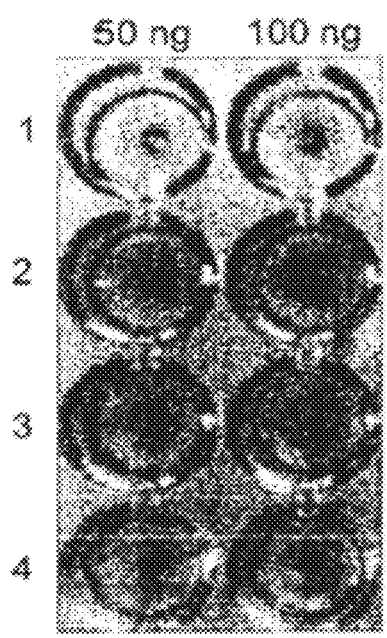

FIG. 5 shows immunoprecipitates which were resuspended and analysed by western blotting using the anti-His antibody. Buffers used for the immunoprecipitation were PBS (lanes 1, 2, 9, 10), PBS-Tween (0.01%) (lanes 3, 4), PBS-NP40 (0.1%) (lanes 5, 6), PBS-Triton (0.5% (lanes 7, 8). Serum samples containing anti-HPA-1a antibody (1, 3, 5, 7) or not (2, 4, 6, 8) were used for immunoprecipitations. Negative controls without Trx-HPA-1a (9) or without immunoglobulins (10) are shown.

FIG. 6 shows the result of a typical immunocapture experiment. The following serums were used: two samples containing anti-HPA-1a antibody (1-2), one sample containing anti-HPA-1b antibody (3), one negative control (4). Wells were coated with 50 or 100 ng of Trx-HPA-1a protein. Interaction with Trx-HPA-1a is only detected with serums containing the anti-HPA-1a antibody (1, 2).

Figure 7:
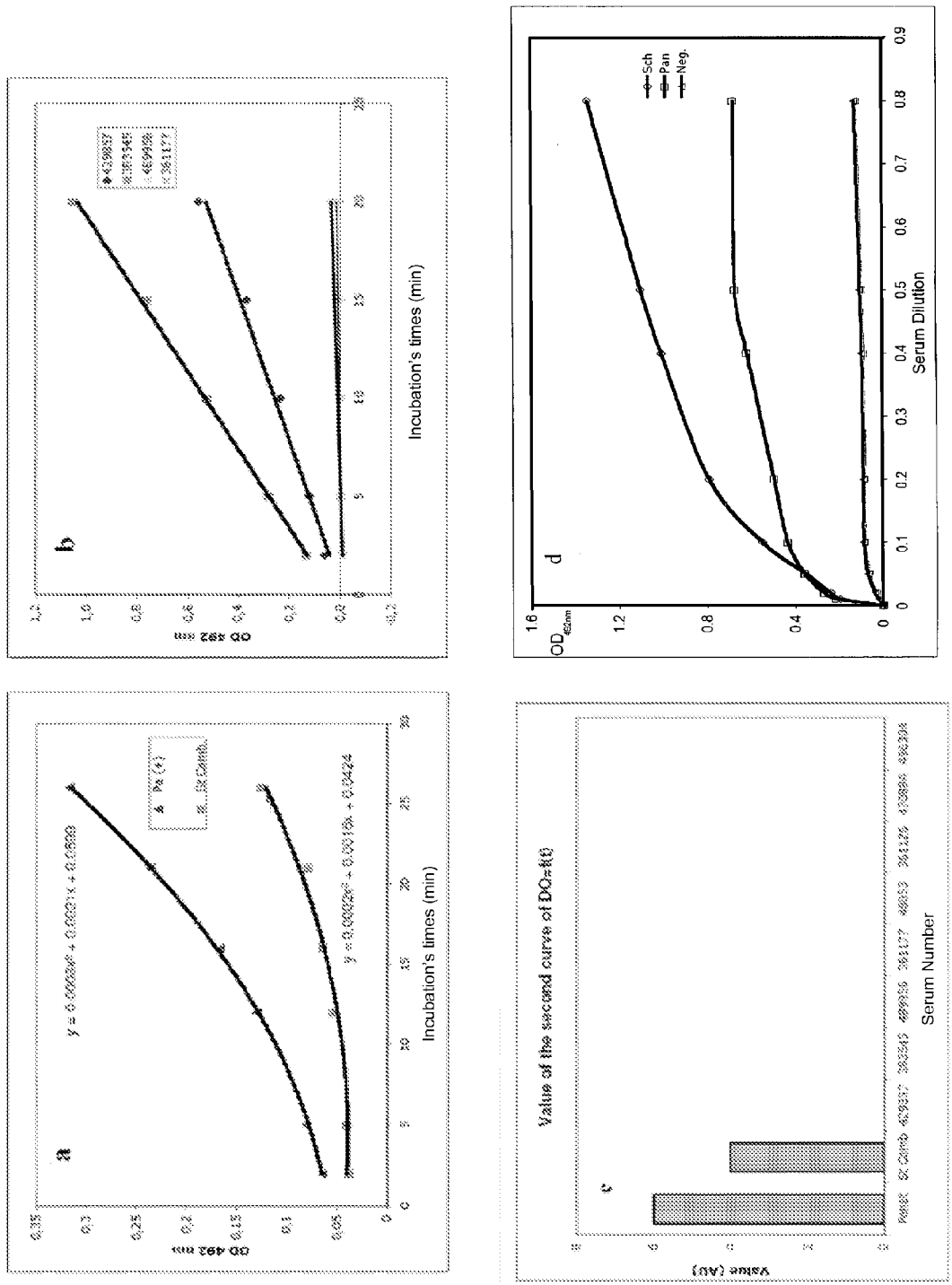

FIG. 7 shows ELISA experiments. Time course analysis of OD at 492 nm. Serum containing (P+ and St Camb) (7a) or not (429876, 383545, 489956, 361177) (7b) anti-HPA-1a antibody were used. The value of $d^2OD/dt^2$ is shown (7c). Calculation of $d^2OD/dt^2$ allows to discriminate between positive and negative samples.

FIG. 7d shows the detection of HPA-1a specific antibodies in human sera which was determined by an ELISA assay using microtitration plates (Nunc) coated overnight at 4° C. with 150 ng of Trx-HPA-1a per well in carbonate buffer. The plates were rinsed two times with 200 μL PBS. Nonspecific binding was blocked by placing 200 μL PBS containing 1% bovine serum albumin (BSA) (A7030, Sigma) for 100 minutes at room temperature (RT). Then, the plates were rinsed one time with 200 μL PBS and again incubated for 45 min at RT on shaking incubator with human sera diluted (1:100 to 4:5) in 100 μl PBS+1% BSA. After three washes with PBS containing 0.05% Tween 20 and one washes with PBS, the plates were incubated for 40 min at RT on a shaking incubator with HRP-conjugated Goat Anti-Human IgG, Fc fragment specific (Jackson ImmunoResearch). After three washes with PBS+0.05% Tween 20 and two washes with PBS, the binding of anti-HPA-1 antibody was detected by addition of peroxidase substrate (OPD:1,2-phenylenediamine dihydrochloride) according to manufacturer's instructions (DakoCytomation). 20 min later, the reaction was stopped by adding 100 μL 0.5 M $H_2SO_4$. The absorption was registered at 492 nm with ELISA plate reader. The OD evolution at 492 nm depends on anti HPA-1a titer in the serum. This evolution is characteristic for the antibody-antigen interaction, demonstrating that the Trx-HPA-1a aptamer can distinguish serum with or without anti-HPA-1a. Samples named Sch and Pan contained anti-HPA-1a antibody while sample Neg is a negative control from healthy donor. For high dilution (1/50) the OD is <0.05 for Neg. Serum whereas OD>0.23 for Sch and Pan. The situation is the same at low dilution (½) with the OD<0.11 for Neg. and >0.66 for Sch and Pan.

Figure 8A:
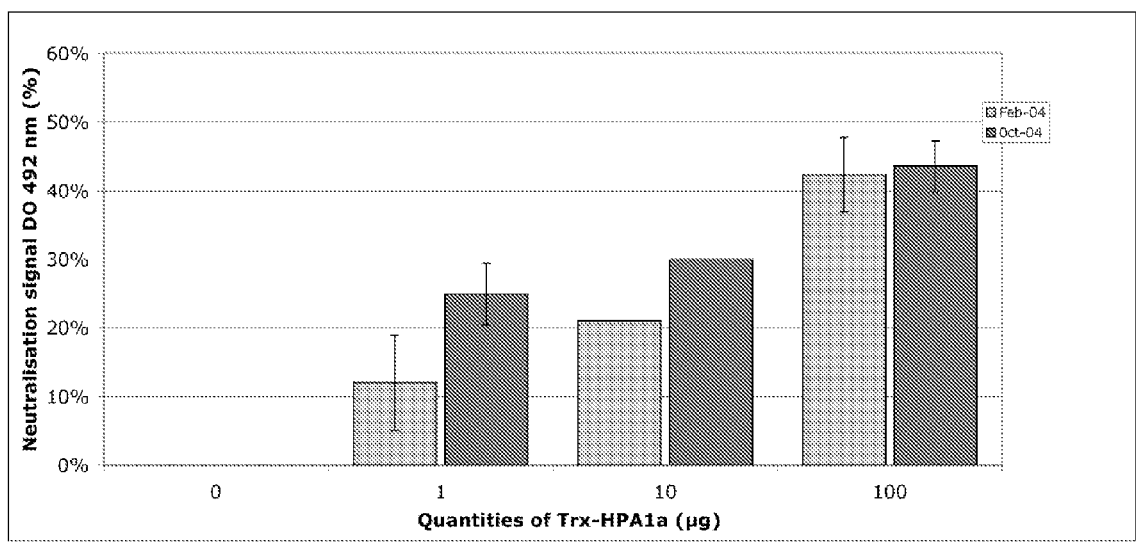
Figure 8B:
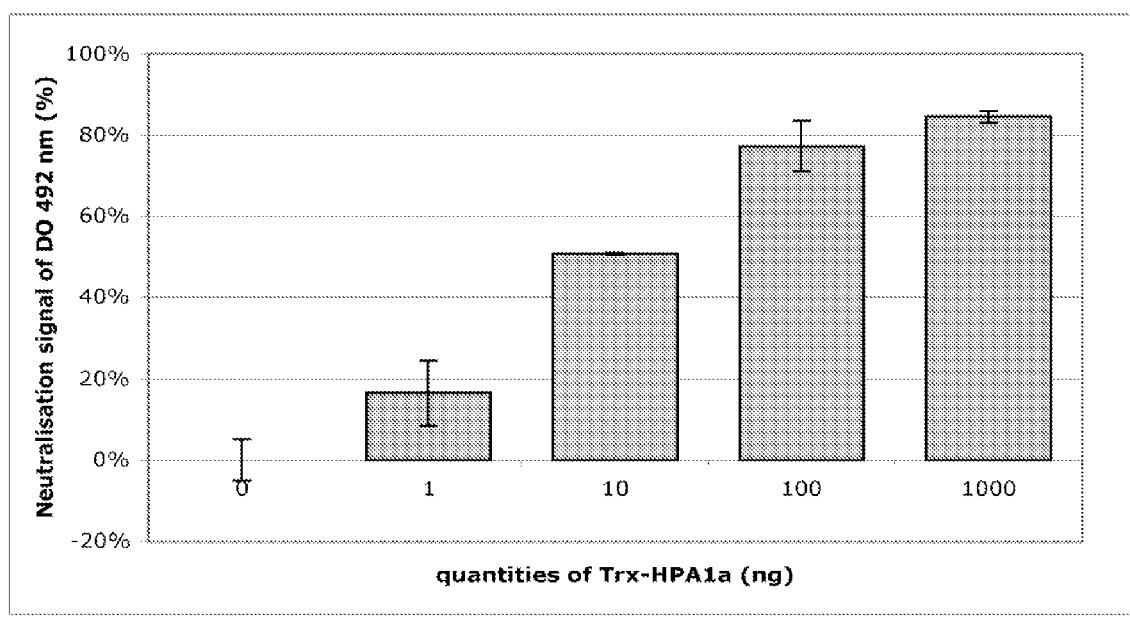
Figure 8C:
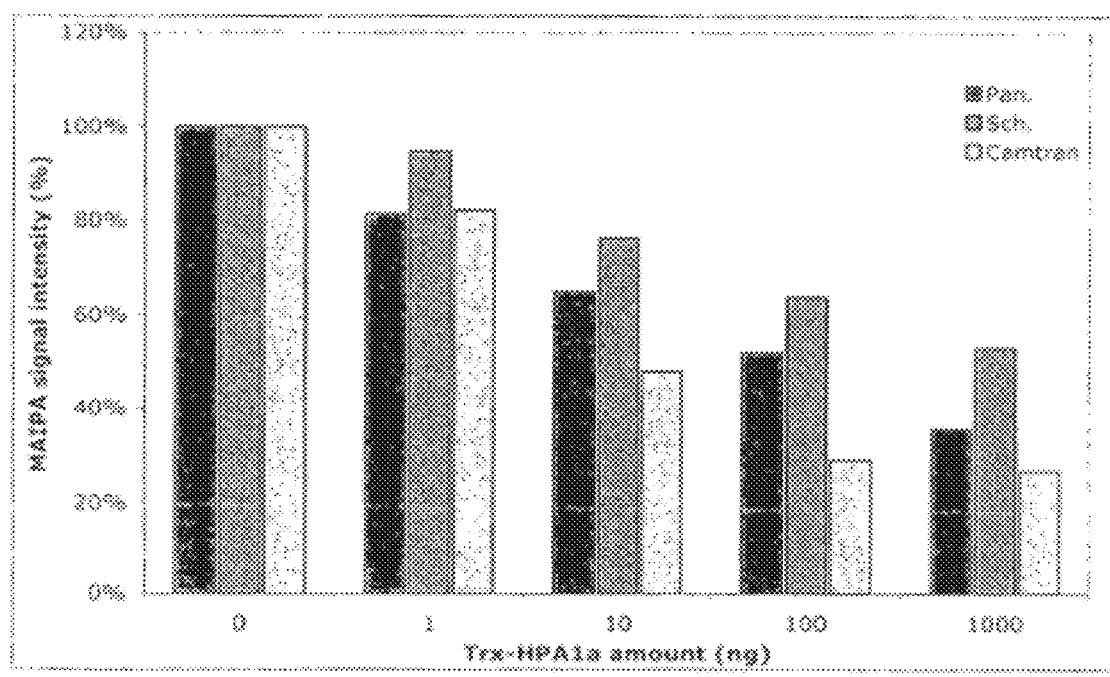

FIG. 8 shows (a) the neutralisation of alloantibodies anti-HPA-1a of human serum in MAIPA assay. Two different dates of production were use to compare stability in time, (b) the neutralisation of Camtran antibody in MAIPA assay with Trx-HPA-1a. 100 ng of Trx-HPA-1a is sufficient to inhibit Camtran in MAIPA assay and (c) the neutralisation of 2 human sera containing specific HPA-1a antibodies (anti-HPA-1a).

EXAMPLES

Example 1

FliTrx™ Peptide Library and Monoclonal Antibody

The FliTrx™ random peptide library, based on the system described by Lu et al. (Lu Z, Murray K S, Van Cleave V, LaVallie E R, Stahl M L, McCoy J M. Expression of thioredoxin random peptide libraries on the Escherichia coli cell surface as functional fusions to flagellin: a system designed for exploring protein-protein interactions. Biotechnology (N Y). 1995 April; 13(4):366-72), was obtained from Invitrogen (San Diego, Calif.). A mAb Camtran against GPIIb/IIIa protein specific to phenotype HPA-1a was obtained from Cambridge (Griffin H. M., Ouwehand W. H., A human monoclonal antibody specific for the Leucine 33 (HPA-1a) form of platelet glycoprotein IIIa from V gene phage display library, Blood 1995, 86, 12:4430-4436).

Growth and Induction of Peptide Library

Cell cultures and general panning methods are conducted as described in the manufacturer's protocol. pFliTrx™ which contains the PL bacteriophage promoter to drive expression is propagated in E. coli (G1826) in which expression of the cl repressor is under the control of the trp promoter. The E. coli cells harboring the plasmids, are grown to saturation overnight at 25° C. in IMC medium (1×M9 salts (40 mM $Na_2HPO_4$, 20 mM $KH_2PO_4$, 8.5 mM NaCl, 20 mM $NH_4Cl$), 0.2% casamino acids, 0.5% glucose, 1 mM $MgCl_2$) containing 100 μg/ml ampicillin. Expression of the thioredoxin-flagellin fusion proteins containing the peptide inserts is induced by 100 μg/ml tryptophan for 6 h at 25° C. A mixture of 0.1 g of non-fat dry milk, 300 μl of 5 M NaCl and 500 μl 20% α-methyl mannoside is then added to 10 ml of the induced E. coli culture. The resulting solution is used as a peptide library ready for screening as follows.

Panning of the Random Peptide Display Library 60 mm tissue culture plates (Nunc) are used for peptide library screening. Plates are precoated for one hour at 20-25° C. with 20 μg of antibody diluted in 1 ml sterilized water. After the liquid is removed, the plates are washed with 10 ml sterile water and then supplemented with 10 ml of blocking solution (1% non-fat dry milk, 150 mM NaCl, 1% α-methyl mannoside and 100 μg/ml ampicillin in IMC medium), gently agitating for 1 h. Just before the end of the 6 h induction of peptide library, the blocking solution is decanted and 10 ml aliquots of the resulting solution are added to the plates. The plates are gently agitated at 75 rpm on a horizontal shaker for 1 min and incubated for 1 h at 20-25° C. The bacterial culture is decanted and the plates are washed by gently agitating for 5 min with 10 ml of IMC medium containing 100 μg/ml ampicillin and 1% α-methyl mannoside. After washing an additional four times, bound bacteria are detached with 1 ml IMC by vortexing for 30 s. The remaining detached bacteria are collected from the plate and grown for the next round of biopanning. The same procedure is performed in the subsequent four biopanning rounds. After five rounds of biopanning, the bacterial colonies are randomly picked from the RMG (1×M9 salts, 2% casamino acids, 0.5% glucose, 1 mM $MgCl_2$, 100 μg/ml ampicillin and 1.5% agar) plates, and grown overnight at 30° C.

Western Blotting

Identification of positive clones by Western blotting is done essentially according to the manufacturer's protocol. Briefly, fourty clones of the RMG plate are transferred into 2 ml RM medium (1×M9 salts, 2% casamino acids, 1% glycerol, 1 mM $MgCl_2$) containing 100 μg/ml ampicillin), and grown to saturation at 30° C. with shaking. A 40 μl sample from the overnight culture is inoculated at 37° C. in 2 ml IMC containing 100 μg/ml ampicillin and 100 μg/ml tryptophan until the cell density is OD 600 0.75. A 1.5 ml aliquot of induced cell culture is harvested and centrifuged at 10.000 g for 1 min. The pellet is resuspended in SDS-polyacrylamide gel-loading buffer, boiled for 5 min and electrophoresed in 8% SDS-polyacrylamide gel. The separated proteins are blotted onto a nitrocellulose membrane (PROTRAN® BA79, Schleicher & Schuell) in a liquid electrophoretic transfer cell (Bio-Rad). Membranes are then blocked with TBS (10 mM Tris pH 7.2 and 0.15 M NaCl) 5% dry milk overnight at 4° C., then incubated with camtran antibody, diluted 1:100 in TBS 1% dry milk, 0.05% Tween 20, for 2 h at 20-25° C. After being washed three times with TBS 0.05% Tween 20, membranes are then incubated with horseradish peroxidase (HRP)-conjugated goat anti-human IgG Fc specific (Sigma A0170) diluted 1:92000 for 40 min at 20-25° C. After a further three washes with TBS 0.05% Tween20, bound conjugate is detected by Lumi-LightPLUS Western Blotting Substrate (Roche). Positive clones are then re-analyzed by Western blotting carried out with a human serum reacting against the GPIIb/IIIa protein which is specific to the HPA-1b phenotype.

DNA Sequencing

Plasmid DNAs of the identified clones are isolated using Wizard® Plus SV Minipreps DNA Purification System (Promega). The nucleotide sequences are determined by MWG using the FliTrx™ Forward sequencing primer (5'-ATTCACCTGACTGACGAC-3').

Cloning, Expression and Purification of Protein Trx-HPA-1a

Cloning and Generation of the Expression Plasmid

A cDNA encoding thioredoxin-peptide is amplified by PCR reaction using the pFlitrx plasmid selected previously. PCR conditions are as follows: 1 min at 95° C., followed by 12 cycles at 95° C. 45 s, 36° C. 30 s, 72° C. 45 s, then 20 cycles 95° C. 45 s, 45° C. 30 s, 72° C. 45 s and 72° C. for 3 min to fill in the flush. At the 3'-end, the primer sequence 5'-TGTCGAC-CAGGTTAGCGTC-3' introduces a SalI site, and at the 5'-end, the primer sequence 5'-TCATATGATGAGC-GATAAAATTA-3' introduces a NdeI site. The PCR generated DNA fragment is subcloned into the pGEM®-T Easy Vector System I (Promega). Then plasmid construct is amplified and digested by restriction enzyme NdeI and SalI. The digested DNA fragment is cloned into the NdeI and SalI sites of the ampicillin-resistant vector pT7-7 (a vector based on the T7 polymerase expression system) encoding six His codons followed by a stop codon downstream of the SaltI site. The plasmid is transformed into Escherichia coli strain DHSa, and ampicillin-resistant colonies are isolated. Resistant colonies are grown to allow large-scale production and purification of the plasmid. Proper construction of the plasmid is confirmed by DNA sequencing.

Overexpression and Purification of Trx-HPA-1a (JT-PLP01)

The plasmid is transformed into E. coli strain C41(DE3) (Miroux B, Walker J E. Over-production of proteins in Escherichia coli: mutant hosts that allow synthesis of some membrane proteins and globular proteins at high levels. J Mol Biol. 1996 Jul. 19; 260(3):289-98). A freshly transformed colony is inoculated into 400 mL of 2YT medium (16% Bacto Tryptone, 10% Bacto YeastExtract, 85.5 mM NaCl) containing 20 μg/ml ampicillin and grown at 37° C. to an OD600 of 0.6-0.8 before induction with 0.7 mM isopropyl b-D thiogalactopyranoside. After overnight incubation at 37° C., cells are harvested by centrifugation. The pellet is suspended and incubated for 30 min at 4° C. in 10 mL of lysis buffer (20 mM Tris-HCl pH 8.0, 20% glycerol, 500 mM NaCl, 0.1% Triton X-100, 1 mM PMSF, 1 mg/mL lysozyme, ½ tablet Complete Mini EDTA-free (Roche) and 250 units/mL Benzonase (Merck)). Fractions (5 ml) are disrupted by sonication for 30 s. After four rounds of centrifugation of the supernatants (9000 g for 30 min), the soluble fraction is applied onto an 7 ml Ni—NTA-agarose column (Qiagen) equilibrated previously in lysis buffer without lysozyme and Benzonase. Mixture is incubated in bath at 4° C., for 1 hour. The column is washed with lysis buffer without lysozyme and Benzonase and then with 20 mM Tris-HCl pH 8.0, 20% glycerol, 100 mM KCl, 0.5 mM PMSF, and 20 mM imidazole, Trx-HPA-1a is eluted with the same buffer containing 100 mM imidazole. Fractions containing Trx-HPA-1a as judged by SDS-PAGE are pooled. The buffer of the samples is exchanged and the sample is concentrated by centrifugation with Vivaspin Concentrator membrane (Vivascience) cutoff of 5 kDa and 20 mM Tris pH 8.0, 10 mM NaCl. Samples are applied to 1 mL Q-Sepharose columns (Mono Q HR 5/5, Amersham Pharmacia Biotech). The column is washed with 20 mM Tris pH 8.0, 10 mM NaCl, and Trx-HPA-1a is eluted with a linear gradient of 10 mM to 1 M NaCl. Trx-HPA-1a rich fractions were pooled, concentrated to 1-15 mg/ml, equilibrated in PBS or sterilized water on Vivaspin Concentrator and stored at −20° C. until they are used. Protein concentrations are determined by the Bradford method (Kruger N J. The Bradford method for protein quantitation. Methods Mol. Biol. 1994; 32:9-15).

Analysis of Purified Trx-HPA-1a

Mass spectra are acquired using an electrospray API 165 (Applied Biosystems) instrument. The identity is established by peptide mass fingerprinting and Maldi-Tof analysis (voyager—DE TM PRO, Applied Biosystems).

Purification of Total IqG from Human Sera

The human sera equilibrated with 10% 1 M Tris-HCl pH 8 is applied onto an 250 μl ml protein A-sepharose beads column (P3391, Sigma-Aldrich) equilibrated previously in 100 mM Tris-HCl pH 8. The column is washed with ten volumes of 100 mM Tris-HCl pH 8 and ten volumes of 10 mM Tris-HCl pH 8. Total IgG is eluted with 100 mM glycine pH 3. Elution fractions are neutralized with 10% 1M Tris-HCl pH 8. Fractions containing IgG are concentrated and the buffer is exchanged on a Vivaspin Concentrator membrane cutoff of 5 kDa and PBS. Samples are analyzed in SDS-PAGE and IgG concentrations are determined by the Bradford method (Kruger N J. The Bradford method for protein quantitation. Methods Mol. Biol. 1994; 32:9-15).

Example 2

Co-Immunoprecipitation.

1 μg Trx-HPA-1a protein is incubated with 30 μg IgG extract from human sera in buffer A (PBS 0.5 M trehalose) or buffer A with 0.01% Tween 20 or with 0.1% NP40 or with 0.05% Triton for 2 h at 20-25° C. 10% 1 M Tris-HCl is added to the mixture and incubated with 25 μl of protein A—sepharose beads previously equilibrated in 100 mM Tris-HCl pH 8 at 4° C. 45 min. The beads are then washed three times with 100 mM Tris-HCl pH 8, 0.2% Tween 20 at 4° C. 10 min and then three times with 10 mM Tris-Hcl pH 8, 0.2% Tween 20. To make the proteinA-sepharose-IgG-Trx-HPA-1a complex fall, the mixture is centrifuged 2 min at 10 000 g. Proteins are eluted by boiling in SDS sample buffer and the eluate is resolved on a 15% SDS-polyacrylamide gel and blotted onto a nitrocellulose membrane (PROTRAN® BA79, Schleicher & Schuell) in a liquid electrophoretic transfer cell. The membranes are then blocked with TBS 5% dry milk at 4° C. overnight, then incubated with anti-His antibody (His-probe, Santa Cruz Biotechnology), diluted 1:200 in TBS 1% dry milk, 0.05% Tween 20 for 1 h10 at 20-25° C. After three washes with TBS 0.05% Tween 20, membranes are then incubated with HRP-conjugated goat anti-rabbit IgG (Dakocytomation) diluted 1:3000 for 50 min at 20-25° C. After a further three washes with TBS 0.05% Tween 20, bound conjugate is detected by Lumi-LightPLUS Western Blotting Substrate.

Example 3

Immunocapture

Immunocapture is a classical technique to detect IgG antibodies directed against platelets according to the technique published by Rachel et al. (Med Lab Sci: 1985, 42; 194-199).

Herein, Interaction between Trx-HPA-1a and human sera containing Ab against platelet HPA-1a is tested by immunocapture. A solid phase system for the detection of IgG Antibodies to platelets assay is used (Capture P®, Immucor). The pool of platelets is replaced by Trx-HPA-1a protein. Microtitration plates with conics well are coated overnight at 4° C. with 50 ng or 100 ng of Trx-HPA-1a per well in carbonate buffer (15 mM $Na_2CO_3$, 35 mM $NaHCO_3$ in deionised water). After washing with PBS, 50 μl serum of anonymous donor is added into the wells and incubated at 37° C. for 45 min. After six washes, 50 μl of Capture-P indicating erythrocytes (red blood cell carrying anti-human IgG antibody).

Example 4

Immunoassay

The detection of HPA-1a specific antibodies in human sera is determined by an ELISA test using microtitration plates (Nunc) coated overnight at 4° C. with 100 ng of Trx-HPA-1a per well in carbonate buffer. The plates are rinsed two times with 250 μL PBS. Nonspecific sites are blocked by a 1 h 30 min incubation at 20-25° C. with 250 μl PBS containing 1% bovine serum albumin (BSA) (A7030, Sigma). The plates are rinsed one time with 250 μL PBS and then incubated for 45 min at 20-25° C. on a shaking incubator with 10 μl of human sera diluted in 100 μl PBS 1% BSA. After three washes with PBS containing 0.05% Tween 20 and one wash with PBS, the plates are incubated for 40 min at 20-25° C. on a shaking incubator with HRP-conjugated Goat Anti-Human IgG, Fc fragment specific (Jackson ImmunoResearch). After three washes with PBS 0.05% Tween 20 and two washes with PBS, the binding of the anti-HPA-1 antibody is detected by addition of peroxidase substrate OPD (1,2-phenylenediamine dihydrochloride) (DakoCytomation) according to manufacter's instruction. Absorption is measured at 492 nm and followed during 25-30 min using ELISA plate reader. To stop reaction 100 μl 0.5 M $H_2SO_4$ is added on the well. Then the curve of evolution of absorbance according to the incubation's times of OPD is analyzed.

Example 5

In this experiment, the ability of Trx-HPA-1a to neutralize the binding of human IgG HPA-1a specific polyclonal alloantibodies is determined by the MAIPA technology. The MAIPA technology is used as described by Kiefel et al. (Blood: 1987, 70; 1722-1727). The MAIPA technology is a more specific technique to detect and identify platelets' allo-and autoantibodies.

In particular, 50 μL of human serum containing or not polyclonal anti-HPA-1a or 15 ng of Camtran in 50 μL human serum without polyclonal anti-HPA-1a is incubated for 25 min at 20-25° C. with shaking incubator with 0, 1 ng, 10 ng, 100 ng or 1000 ng of Trx-HPA-1a diluted in 20 μL PBS. The mixture is preincubated 5 min with 3 μl of Ni—NTA agarose beads and the complex alloantibodies/Trx-HPA-1a is pulled down by centrifugation 13000 rpm, 2 min. 50 μl of supernatant is used to perform the MAIPA. The neutralization of serum is then determined as usual using the MAIPA technique.

Increasing concentrations of Trx-HPA-1a (0, 1 ng, 10 ng, 100 ng and 1000 ng) diluted in 30 μL PBS are added to 50 μL of human serum containing or not polyclonal anti-HPA-1a or 15 ng of Camtran diluted in 50 μL human serum without polyclonal anti-HPA-1a. After incubation at 20-25° C. for 25 min, the mixture is pre-incubated with 3 μl of Ni—agarose beads and the complex alloantibodies or Camtran/Trx-HPA- 1a is pulled down by centrifugation at 13000 rpm for 2 min. The neutralization of 50 µsupernatant serum is then determined as usual using the MAIPA technique. The results are shown in FIGS. 8a, b and c.

Example 6

Detection of Anti-HPA-1a Antibodies Using MAIPA and ELISA

Blood samples (Table 1, left) are from anonymous donors or from NAIT patients. MAIPA is performed on either crude serum (Table 1, "MAIPA") or protein A-purified immunoglobulins (Table 1, "MAIPA pure"). The vast majority of donors is found negative using both MAIPA and ELISA. Seven samples found to be negative with MAIPA exhibit an optical density above 0.1 (OD>0.1) with ELISA (end point measurement). However, for all donor samples, time course analysis show that optical density increases linearly with time, the primary derivative being constant (dOD/dt=constant) and the secondary derivative being equal to zero ($d^2OD/dt^2=0$). Therefore a given sample is indexed as negative using ELISA if $d^2OD/dt^2=0$. Results of ELISA time course analyses are displayed in the indicated column (Table 1, "Curve"): donor samples are all tested negative ($d^2OD/dt^2=0$), while the three tested samples from NAIT patients (Pan, St Camb, Bru) are found positive ($d^2OD/dt^2>0$). Consequently, a given sample is negative with the ELISA decribed herein if it fulfills one of the following criteria: optical density below 0.1 (end point) or $d^2OD/dt^2=0$ (time course). It should be pointed out that all samples found to be negative with the end point protocol, are found negative with the time course protocol as well. In addition, immuno-depletion of three samples from NAIT patients (Pan, Sch, Ac mB2) is successfully carried out with the purified peptide aptamer (Table 1, "neutr."). Genotyping for HPA locus is shown (Table 1, "geno.").

Table 1 shows the summarized results from the anti-HPA-1a antibody detection experiments using MAIPA and ELISA. The symbols are as follows: (−) negative; (+) positive; (−/+) first tested negative but positive later on; (ND) not determined.

TABLE 1

| Sample number | MAIPA | MAIPA pure | ELISA | Slope Curve | neutr. | geno. |
|---|---|---|---|---|---|---|
| Donors: (n = 115) | | | | | | |
| 1 to 103 | − | ND | − | ND | | |
| 104 to 108 | − | ND | − | − | | |
| 109 | − | − | OD > 0.1 | − | | a/a |
| 110 | − | − | OD > 0.1 | − | | a/a |
| 111 | − | − | OD > 0.1 | − | | a/a |
| 112 | − | ND | OD > 0.1 | − | | ND |
| 113 | − | − | OD > 0.1 | − | | a/a |
| 114 | − | − | OD > 0.1 | − | | a/a |
| 115 | − | − | OD > 0.1 | − | | a/a |
| Patients: (n = 27) | | | | | | |
| Pen | − | − | − | | | ND |
| Tro | − | − | − | | | ND |
| Hal | − | − | − | | | ND |
| Bra1 | − | − | − | | | ND |
| Per | − | − | − | | | ND |
| Ama | − | − | − | | | ND |
| Del | − | − | − | | | ND |
| Pas | − | − | − | | | ND |
| Par | − | − | − | | | ND |
| Bra2 | − | − | − | | | ND |
| Pie | − | − | − | | | ND |
| Jas | − | − | − | | | ND |
| Gar | − | − | + | | | ND |
| LeM | − | + | + | | | ND |
| DeA | −/+ | + | + | | | α 2b3a |
| And | − | + | + | | | |
| Mar | − | + | + | | | |
| Bou | − | + | + | | | |
| Cha | − | + | + | | | |
| Pro | + | + | + | | | α glyco |
| Dum | + | + | + | | | α 3a |
| Pan | + | + | + | + | + | b/b |
| Kurc | + | + | + | | | |
| St Camb | + | ND | + | + | | |
| Sén | + | + | − | | | b/b |
| Sch | + | | | | + | ND |
| Bru | + | | + | + | | b/b |
| Ac mB2 | | + | + | | + | |

The invention claimed is:

1. A nucleic acid containing a nucleotide sequence encoding a peptide aptamer comprising:

(A) at least one dodecapeptide having in the direction of N-terminus to C-terminus a sequence of SEQ ID NO: 1;

(B) at least one polypeptide; and (C) one or more detectable marker(s), wherein the peptide aptamer mimics human platelet antigen HPA-1a epitope present on glycoproteins GPIIb/IIIa.

2. The nucleic acid according to claim 1, wherein the polypeptide is selected from the group consisting of thioredoxin (Trx), green fluorescent protein (GFP), Staphylococcal nuclease, coiled coil polypeptides, cysteine-containing polypeptides that form disulfide bridges or one or more fragments thereof.

3. A nucleic acid containing a nucleotide sequence encoding a peptide aptamer comprising:

(A) at least one dodecapeptide having in the direction from N-terminus to C-terminus a sequence of:

(i) four aliphatic amino acids selected from the group consisting of valine, isoleucine, leucine, alanine and glycine, (ii) two acid amino acids selected from the group consisting of aspartic acid and glutamic acid, (iii) one proline, (iv) one basic amino acid selected from the group consisting of arginine, lysine and histidine, (v) two acid amino acids selected from the group consisting of aspartic acid and glutamic acid, (vi) one alcohol amino acid selected from the group consisting of threonine and serine and (vii) one aromatic amino acid selected from the group consisting of tryptophan, tyrosine and phenylalanine;

(B) at least one polypeptide; and (C) one or more detectable marker(s), the detectable marker(s) is/are selected from the group consisting of fluorescent marker, radioactive marker, His-tag, glutathione transferase (GST), Flag-tag, biotin, Ha-tag, Myc-tag and XPress-tag, wherein the peptide aptamer mimics human platelet antigen HPA-1a epitope present on platelet glycoproteins GPIIb/IIIa.

* * * * *